(12) United States Patent
Richard et al.

(10) Patent No.: US 9,415,012 B2
(45) Date of Patent: Aug. 16, 2016

(54) SUSTAINED-RELEASE COMPOSITION CONTAINING PEPTIDES AS ACTIVE INGREDIENT

(75) Inventors: Joël Richard, Méré (FR); Faïza Laredj, Uccle (BE); Marie-Madeleine Baronnet, Ezy sur Eure (FR); Didier Nourrisson, Vernouillet (FR); Jeremiah Harnett, Gif-sur-Yvette (FR); Béatrice Hacher, Angerville la Campagne (FR); Nathalie Mondoly, Le Chesnay (FR); Laurent Bertocchi, Sylvains les Moulins (FR)

(73) Assignee: IPSEN PHARMA S.A.S., Boulogne-Billancourt (FR)

( * ) Notice: Subject to any disclaimer, the term of this patent is extended or adjusted under 35 U.S.C. 154(b) by 0 days.

(21) Appl. No.: 14/126,365

(22) PCT Filed: Jun. 13, 2012

(86) PCT No.: PCT/IB2012/001588
§ 371 (c)(1),
(2), (4) Date: Dec. 13, 2013

(87) PCT Pub. No.: WO2012/172433
PCT Pub. Date: Dec. 20, 2012

(65) Prior Publication Data
US 2014/0127303 A1 May 8, 2014

(30) Foreign Application Priority Data
Jun. 14, 2011 (EP) .................................... 11290270

(51) Int. Cl.
*A61K 38/33* (2006.01)
*A61K 9/16* (2006.01)
*A61K 9/00* (2006.01)

(52) U.S. Cl.
CPC ............. *A61K 9/1652* (2013.01); *A61K 9/0019* (2013.01); *A61K 38/33* (2013.01)

(58) Field of Classification Search
None
See application file for complete search history.

(56) References Cited

U.S. PATENT DOCUMENTS

| 5,821,221 A | 10/1998 | Shalaby |
| 8,039,435 B2 | 10/2011 | Dong |
| 9,296,783 B2 | 3/2016 | Dong |
| 2002/0197328 A1 | 12/2002 | Kim et al. |
| 2011/0189299 A1 | 8/2011 | Okubo et al. |

FOREIGN PATENT DOCUMENTS

| CN | 1222857 A | 7/1999 |
| CN | 102083419 A | 6/2011 |
| GB | 761 061 A | 11/1956 |
| JP | 2009-500427 | 1/2009 |
| JP | 2010-528018 | 8/2010 |
| WO | 9843664 A1 | 10/1998 |
| WO | WO 01/00224 | 1/2001 |
| WO | WO 2008/156677 | 12/2008 |
| WO | WO 2009/061411 | 5/2009 |
| WO | WO 2011/017209 | 2/2011 |
| WO | WO 2011/060352 | * 5/2011 |

OTHER PUBLICATIONS

Huang, Jian-Yan et al., "Synthesis of Agarose-*graft*-Hyaluronan Copolymer and Its Potential Application as a Peptide Carrier", J. of Appl. Polym. Sci. (2010), vol. 117, No. 6, pp. 3568-3574.
International Search Report issued in PCT/IB2012/001588 (4 pages).
Chinese Office Action for Chinese Patent Application No. 201280029159.5 dated Dec. 3, 2014.
Kilpelainen et al., European Journal of Pharmaceutics and Biopharmaceutics, 77: 20-25 (2011).
Kim et al., Journal of Controlled Release, 104:323-335 (2005).
Hahn et al., Pharmaceutical Research, 21: 1374-1381 (2004).
"Igaku no ayumi" (Journal of Clinical and Experimental Medicine), 233:736-742 (2010).
"Tounyoubyou" (Diabetes), 46:29-33 (2003).
The Journal of the Japanese Society of Internal Medicine, 89:2010-2018 (2000).

* cited by examiner

*Primary Examiner* — James H Alstrum Acevedo
*Assistant Examiner* — Roy Teller
(74) *Attorney, Agent, or Firm* — Hunton & Williams LLP

(57) ABSTRACT

The present invention relates to a sustained-release drug composition consisting essentially of microparticles of a peptide as the active substance and a biocompatible water-soluble polymer, in particular peptide as meianocortin receptor ligand. The present invention relates also to an injection formulation comprising the sustained-release drug composition suspended in an injection medium.

18 Claims, 1 Drawing Sheet

US 9,415,012 B2

SUSTAINED-RELEASE COMPOSITION CONTAINING PEPTIDES AS ACTIVE INGREDIENT

CROSS-REFERENCE TO RELATED APPLICATIONS

This application is the U.S. National Phase of International Patent Application No. PCT/IB2012/001588, filed Jun. 13, 2012, which claims priority to European Application No. EP11290270.5, filed Jun. 14, 2011, the contents of each are hereby incorporated by reference in their entireties.

FIELD OF THE INVENTION

The present invention relates to a sustained-release drug composition consisting essentially of microparticles of a biocompatible water-soluble polymer and a peptide as the active substance, in particular a peptide as melanocortin receptor ligand. The present invention relates also to an injectable formulation comprising the sustained-release drug composition suspended in an injection medium.

BACKGROUND OF THE INVENTION

Melanocortins are a family of regulatory peptides which are formed by post-translational processing of pro-hormone pro-opiomelanocortin. Melanocortins have been found in a wide variety of normal human tissues including the brain, adrenal, skin, testis, spleen, kidney, ovary, lung, thyroid, liver, colon, small intestine and pancreas. Melanocortin peptides have been shown to exhibit a wide variety of physiological activities including the control of behavior and memory, affecting neurotrophic and antipyretic properties, as well as affecting the modulation of the immune system, the control of the cardiovascular system, analgesia, thermoregulation and the release of other neurohumoral agents including prolactin, luteinizing hormone and biogenic amines. Five melanocortin receptors (MC-R) have been characterized to date: melanocyte-specific receptor (MC1-R), corticoadrenal-specific ACTH receptor (MC2-R), melacortin-3 (MC3-R), melanocortin-4 (MC4-R) and melanocortin-5 receptor (MC5-R). There has been great interest in melanocortin (MC-R) receptors as targets for the design of novel therapeutics to treat disorders of body weight such as obesity and cachexia. Both genetic and pharmacological evidence points toward central MC4-R receptors as the principal target. The current progress with receptor-selective agonists and antagonists evidences the therapeutic potential of melanocortin receptor activation, particularly MC4-R. Due to this therapeutic potential, there is a need of new formulations for this type of compounds, in particular a need of injection formulations.

Parenteral injection of a soluble active pharmaceutical ingredient in saline classically leads to a high value of the drug plasma peak concentration ($C_{max}$) and an initial high variation rate of the plasmatic drug concentration that results in a short time ($T_{max}$) to reach the maximal concentration $C_{max}$, i.e. the burst effect. These two features of the pharmacokinetic (PK) profile can induce side effects, which may jeopardise the development and use of the drug.

A composition according to the present invention intends to reduce these drawbacks and allowed a sustained-release of the active ingredient over at least 3 hours.

SUMMARY OF THE INVENTION

The object of the present invention is a sustained-release drug composition consisting essentially of microparticles of a peptide as the active substance and a biocompatible water-soluble polymer.

DETAILED DESCRIPTION OF THE INVENTION

Figure 1:
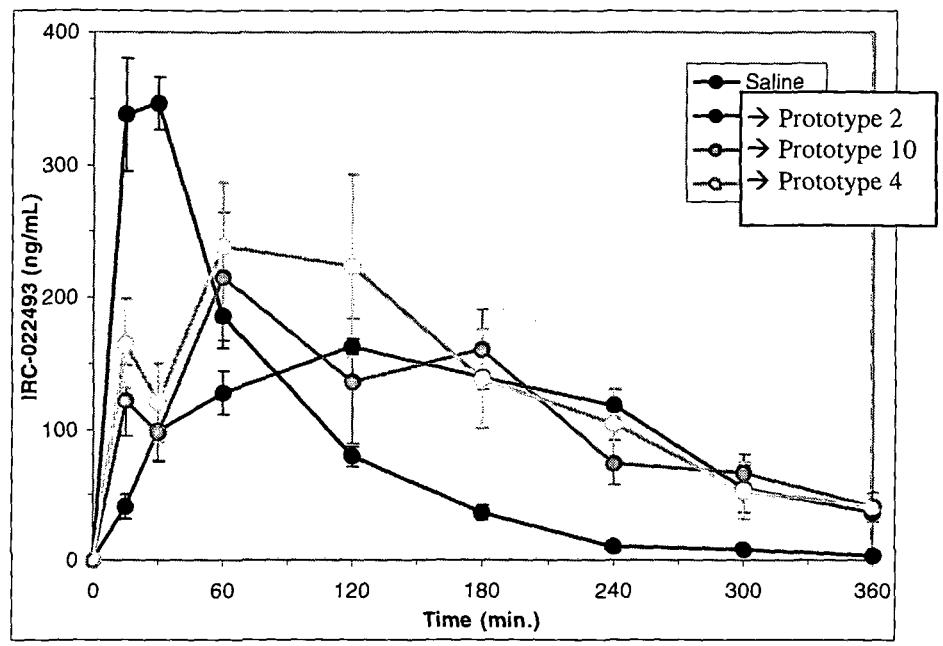
FIG. 1 depicts the pharmacokinetic profiles obtained following the administration of several compositions comprising microparticles of a peptide as compared to that obtained after the injection of the peptide in a saline solution under the same conditions.

Unless otherwise indicated the following definitions are set forth to illustrate and define the meaning and scope of the various terms used to describe the invention herein.

Unless otherwise stated, all percentages mentioned in the present invention are weight percentages (w/w).

The term "microparticles" means particles between 1 and 100 μm in size.

The term "polymer" means a polymer or copolymer or a mixture thereof. The term "biopolymer" means a polymeric substance formed in a biological system.

The term "biocompatible" means biologically compatible by not producing a toxic, injurious, or immunological response in living tissues, biological systems or biological functions.

The term "biodegradable" means capable of being decomposed by biological agents, biological (micro-)organisms, or when placed in biological fluids.

Peptide means a peptide containing up to 50 amino acids and/or with a molecular weight up to about 6,000 Da (6,000±200 Da).

Sustained-release means a release of drug which can occur for at least 2 hours.

The term "high molecular weight" polysaccharide is understood to mean that the polysaccharide used in the composition according to the present invention has a molecular weight (Mw) higher than 1000 kDa.

A sustained-release drug composition consists essentially of microparticles of a peptide as the active substance and of a biocompatible water-soluble polymer. According to the present invention, the term "essentially" means that the percentage (by weight) of the peptide as the active ingredient and of the biocompatible water-soluble polymer is at least 90% of the total composition of the microparticles.

Another object of the present invention is a sustained-release drug composition consisting of microparticles of a peptide as the active substance and a biocompatible water-soluble polymer, the peptide and the biocompatible water-soluble polymer representing at least 90% by weight of the microparticles.

This means that microparticles according to the invention comprise peptide as the active substance and biocompatible water-soluble polymer, the peptide and the biocompatible water-soluble polymer representing at least 90% by weight of the microparticles.

In a preferred embodiment, the percentage of the peptide and of the biocompatible water-soluble polymer is at least 91%, 92%, 93%, 94%, 95%, 96%, 97%, 98% or 99% (w/w) of the total composition of the microparticles.

In another preferred embodiment, the percentage (by weight) of the peptide and of the biocompatible water-soluble polymer is at least 95% of the total composition of the microparticles, and preferably at least 99%, and more preferably at least 99.5%.

The active ingredient of the drug composition of the present invention is a peptide. Preferably, the peptide is a ligand of one or more of the melanocortin receptors (MC-R). The melanocortin receptor may be selected from melanocyte-specific receptor (MC1-R), corticoadrenal-specific ACTH receptor (MC2-R), melacortin-3 (MC3-R), melanocortin-4 (MC4-R) and melanocortin-5 receptor (MC5-R).

The active ingredient of the drug of the composition of the present invention may be selected from those described in the PCT applications WO 2007/008704 or WO 2008/147556.

In a preferred embodiment, the peptide is a ligand of melanocortin-4 receptor (MC4-R).

In a preferred embodiment, the peptide is a compound of formula (I):

$$(R^2R^3)\text{-}A^1\text{-}c(A^2\text{-}A^3\text{-}A^4\text{-}A^5\text{-}A^6\text{-}A^7\text{-}A^8\text{-}A^9)\text{-}A^{10}\text{-}R^1 \quad (I)$$

wherein:

$A^1$ is Acc, HN—$(CH_2)_m$—C(O), L- or D-amino acid or deleted;

$A^2$ is Cys, D-Cys, hCys, D-hCys, Pen, D-Pen, Asp or Glu;

$A^3$ is Gly, Ala, β-Ala, Gaba, Aib, D-amino acid or deleted;

$A^4$ is His, 2-Pal, 3-Pal, 4-Pal, Taz, 2-Thi, 3-Thi or $(X^1,X^2,X^3,X^4,X^5)$Phe;

$A^5$ is D-Phe, D-1-Nal, D-2-Nal, D-Trp, D-Bal, D-$(X^1,X^2,X^3,X^4,X^5)$Phe, L-Phe or D-(Et)Tyr;

$A^6$ is Arg, hArg, Dab, Dap, Lys, Orn or HN—CH$((CH_2)_n$—N$(R^4R^5))$—C(O);

$A^7$ is Trp, 1-Nal, 2-Nal, Bal, Bip, D-Trp, D-1-Nal, D-2-Nal, D-Bal or D-Bip;

$A^8$ is Gly, D-Ala, Acc, Ala, β-Ala, Gaba, Apn, Ahx, Aha, HN—$(CH_2)_s$—C(O) or deleted;

$A^9$ is Cys, D-Cys, hCys, D-hCys, Pen, D-Pen, Dab, Dap, Orn or Lys;

$A^{10}$ is Acc, HN—$(CH_2)_t$—C(O), L- or D-amino acid or deleted;

$R^1$ is —OH or —NH$_2$;

$R^2$ and $R^3$ is, independently for each occurrence, H, $(C_1\text{-}C_{30})$alkyl, $(C_1\text{-}C_{30})$heteroalkyl, $(C_1\text{-}C_{30})$acyl, $(C_2\text{-}C_{30})$alkenyl, $(C_2\text{-}C_{30})$alkynyl, aryl$(C_1\text{-}C_{30})$alkyl, aryl$(C_1\text{-}C_{30})$acyl, substituted $(C_1\text{-}C_{30})$alkyl, substituted $(C_1\text{-}C_{30})$heteroalkyl, substituted $(C_1\text{-}C_{30})$acyl, substituted $(C_2\text{-}C_{30})$alkenyl, substituted $(C_2\text{-}C_{30})$alkynyl, substituted aryl$(C_1\text{-}C_{30})$alkyl or substituted aryl$(C_1\text{-}C_{30})$acyl;

$R^4$ and $R^5$ is, independently for each occurrence, H, $(C_1\text{-}C_{40})$alkyl, $(C_1\text{-}C_{40})$heteroalkyl, $(C_1\text{-}C_{40})$acyl, $(C_2\text{-}C_{40})$alkenyl, $(C_2\text{-}C_{40})$alkynyl, aryl$(C_1\text{-}C_{40})$alkyl, aryl$(C_1\text{-}C_{40})$acyl, substituted $(C_1\text{-}C_{40})$alkyl, substituted $(C_1\text{-}C_{40})$heteroalkyl, substituted $(C_1\text{-}C_{40})$acyl, substituted $(C_2\text{-}C_{40})$alkenyl, substituted $(C_2\text{-}C_{40})$alkynyl, substituted aryl$(C_1\text{-}C_{40})$alkyl, substituted aryl$(C_1\text{-}C_{40})$acyl, $(C_1\text{-}C_{40})$alkylsulfonyl or —C(NH)—NH$_2$;

m is, independently for each occurrence, 1, 2, 3, 4, 5, 6 or 7;

n is, independently for each occurrence, 1, 2, 3, 4 or 5;

s is, independently for each occurrence, 1, 2, 3, 4, 5, 6 or 7;

t is, independently for each occurrence, 1, 2, 3, 4, 5, 6 or 7; and $X^1$, $X^2$, $X^3$, $X^4$, and $X^5$ each is, independently for each occurrence, H, F, Cl, Br, I, $(C_1\text{-}C_{10})$alkyl, substituted $(C_1\text{-}C_{10})$alkyl, $(C_2\text{-}C_{10})$alkenyl, substituted $(C_2\text{-}C_{10})$alkenyl, $(C_2\text{-}C_{10})$alkynyl, substituted $(C_2\text{-}C_{10})$alkynyl, aryl, substituted aryl, OH, NH$_2$, NO$_2$, or CN;

provided that:

(I). when $R^4$ is $(C_1\text{-}C_{40})$acyl, aryl$(C_1\text{-}C_{40})$acyl, substituted $(C_1\text{-}C_{40})$acyl, substituted aryl$(C_1\text{-}C_{40})$acyl, $(C_1\text{-}C_{40})$alkylsulfonyl or —C(NH)—NH$_2$, then $R^5$ is H, $(C_1\text{-}C_{40})$alkyl, $(C_1\text{-}C_{40})$heteroalkyl, $(C_2\text{-}C_{40})$alkenyl, $(C_2\text{-}C_{40})$alkynyl, aryl$(C_1\text{-}C_{40})$alkyl, substituted $(C_1\text{-}C_{40})$alkyl, substituted $(C_1\text{-}C_{40})$heteroalkyl, substituted $(C_2\text{-}C_{40})$alkenyl, substituted $(C_2\text{-}C_{40})$alkynyl or substituted aryl$(C_1\text{-}C_{40})$alkyl;

(II). when $R^2$ is $(C_1\text{-}C_{30})$acyl, aryl$(C_1\text{-}C_{30})$acyl, substituted $(C_1\text{-}C_{30})$acyl or substituted aryl$(C_1\text{-}C_{30})$acyl, then $R^3$ is H, $(C_1\text{-}C_{30})$alkyl, $(C_1\text{-}C_{30})$heteroalkyl, $(C_2\text{-}C_{30})$alkenyl, $(C_2\text{-}C_{30})$alkynyl, aryl$(C_1\text{-}C_{30})$alkyl, substituted $(C_1\text{-}C_{30})$alkyl, substituted $(C_1\text{-}C_{30})$heteroalkyl, substituted $(C_2\text{-}C_{30})$alkenyl, substituted $(C_2\text{-}C_{30})$alkynyl or substituted aryl$(C_1\text{-}C_{30})$alkyl;

(III). either $A^3$ or $A^8$ or both must be present in said compound;

(IV). when $A^2$ is Cys, D-Cys, hCys, D-hCys, Pen or D-Pen, then $A^9$ is Cys, D-Cys, hCys, D-hCys, Pen or D-Pen;

(V). when $A^2$ is Asp or Glu, then $A^9$ is Dab, Dap, Orn or Lys;

(VI). when $A^8$ is Ala or Gly, then $A^1$ is not Nle; and (VII). when $A^1$ is deleted, then $R^2$ and $R^3$ cannot both be H; or a pharmaceutically acceptable salt thereof. In a preferred embodiment, the peptide is a compound of formula (I) wherein $A^1$ is Arg, D-Arg, hArg or D-hArg; or a pharmaceutically acceptable salt thereof.

Preferably the active substance of the drug composition of the present invention is the peptide of formula:

Ac-Arg-c(Cys-D-Ala-His-D-Phe-Arg-Trp-Cys)-NH$_2$ (peptide 1)

peptide 1 or a pharmaceutically acceptable salt thereof.

In a preferred embodiment, the peptide is a compound of formula (II):

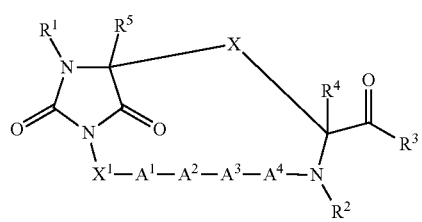
(II)

wherein the hydantoin moiety is formed from fusing the amino group of $X^1$, i.e., wherein:

X is selected from the group consisting of —CH$_2$—S—S—CH$_2$—, —C(CH$_3$)$_2$—S—S—CH$_2$—, —CH$_2$—S—S—C(CH$_3$)$_2$—, —C(CH$_3$)$_2$—S—S—C(CH$_3$)$_2$—, —(CH$_2$)$_2$—S—S—CH$_2$—, —CH$_2$—S—S—(CH$_2$)$_2$—, —(CH$_2$)$_2$—S—S—(CH$_2$)$_2$—, —C(CH$_3$)$_2$—S—S—(CH$_2$)$_2$—, —(CH$_2$)$_2$—S—S—C(CH$_3$)$_2$, —(CH$_2$)$_r$—C(O)—NR$^8$—(CH$_2$)$_t$— and —(CH$_2$)$_r$—NR$^8$—C(O)—(CH$_2$)$_t$—;

$R^1$ and $R^2$ each is, independently for each occurrence thereof, H, (C$_1$-C$_{10}$)alkyl or substituted (C$_1$-C$_{10}$)alkyl;

$R^3$ is —OH or —NH$_2$;

$R^4$ and $R^5$ each is, independently for each occurrence thereof, H, (C$_1$-C$_{10}$)alkyl or substituted (C$_1$-C$_{10}$)alkyl;

$X^1$ is

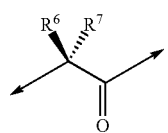

$A^1$ is His, 2-Pal, 3-Pal, 4-Pal, Taz, 2-Thi, 3-Thi, (X$^1$, X$^2$, X$^3$, X$^4$, X$^5$)Phe or deleted;

$A^2$ is D-Bal, D-1-Nal, D-2-Nal, D-Phe or D-(X$^1$, X$^2$, X$^3$, X$^4$, X$^5$)Phe;

$A^3$ is Arg, hArg, Dab, Dap, Lys or Orn;

$A^4$ is Bal, 1-Nal, 2-Nal, (X$^1$, X$^2$, X$^3$, X$^4$, X$^5$)Phe or Trp;

$R^6$ and $R^7$ each is, independently for each occurrence thereof, H, (C$_1$-C$_{10}$)alkyl, (C$_1$-C$_{10}$)heteroalkyl, aryl(C$_1$-C$_5$)alkyl, substituted (C$_1$-C$_{10}$)alkyl, substituted (C$_1$-C$_{10}$)heteroalkyl or substituted aryl(C$_1$-C$_5$)alkyl or $R^6$ and $R^7$ may be joined together form a cyclic moiety;

$R^8$ is H, (C$_1$-C$_{10}$)$_{alkyl}$ or substituted (C$_1$-C$_{10}$)alkyl;

r is, independently for each occurrence thereof, 1, 2, 3, 4 or 5; and t is, independently for each occurrence thereof, 1 or 2; or a pharmaceutically acceptable salt thereof. Preferably the active substance of the drug composition of the present invention is the peptide of formula:

Hydantoin(Arg-Gly))-cyclo(Cys-Glu-His-D-Phe-Arg-Trp-Cys)-NH$_2$ (peptide 2)

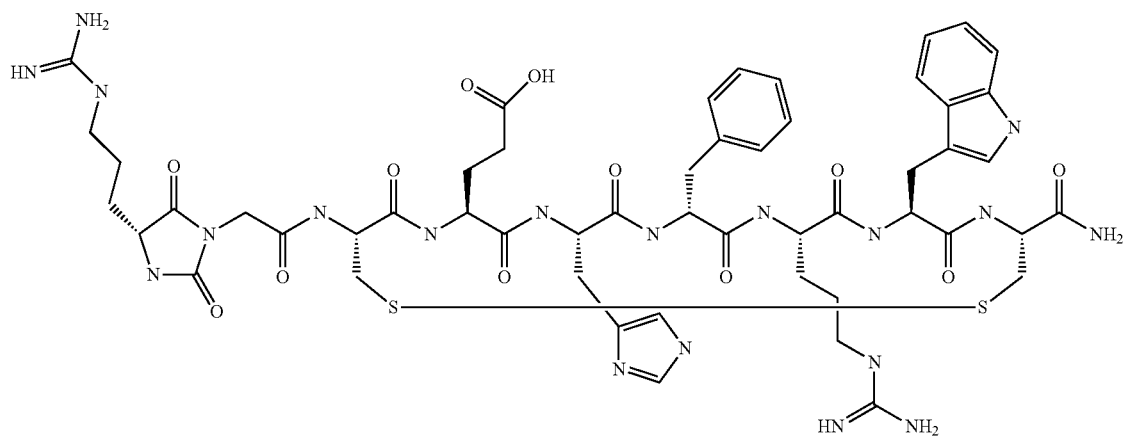

Chiral or a pharmaceutically acceptable salt thereof.

The nomenclature used to define the peptides is that typically used in the art wherein the amino group at the N-terminus appears to the left and the carboxyl group at the C-terminus appears to the right. Where the amino acid has isomeric forms, it is the L form of the amino acid that is represented unless otherwise explicitly indicated. Unless defined otherwise, all technical and scientific terms used herein have the same meaning as commonly understood by one of ordinary skill in the art to which this invention belongs. Also, all publications, patent applications, patents and other references mentioned herein are incorporated by reference. The meaning of the different symbol used above is as follows:

Abu: α-aminobutyric acid; Ac: acyl group; Acc: 1-amino-1-cyclo(C$_3$-C$_9$)alkyl carboxylic acid; A3c: 1-amino-1-cyclopropanecarboxylic acid; A4c: 1-amino-1-cyclobutanecarboxylic acid; A5c: 1-amino-1-cyclopentanecarboxylic acid; A6c: 1-amino-1-cyclohexanecarboxylic acid; Aha: 7-aminoheptanoic acid; Ahx: 6-aminohexanoic acid; Aib: α-aminoisobutyric acid; Ala or A: alanine; β-Ala: β-alanine; Apn: 5-aminopentanoic acid (HN—(CH2)$_4$—C(O); Arg or R: arginine; hArg: homoarginine; Asn or N: asparagine; Asp or D: aspartic acid; Bal: 3-benzothienylalanine; Bip: 4,4'-biphenylalanine, represented by the structure:

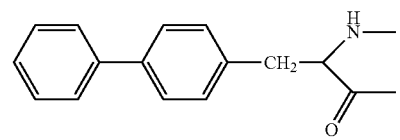 [SMILES: CNC(Cc1ccc(-c2ccccc2)cc1)C(C)=O]

Bpa: 4-benzoylphenylalanine; 4-Br-Phe: 4-bromo-phenylalanine; Cha: β-cyclohexylalanine; hCha: homo-cyclohexylalanine; Chg: cyclohexylglycine; Cys or C: cysteine; hCys: homocysteine; Dab: 2,4-diaminobutyric acid; Dap: 2,3-diaminopropionic acid; Dip: β,β-diphenylalanine; Doc: 8-amino-3,6-dioxaoctanoic acid with the structure of:

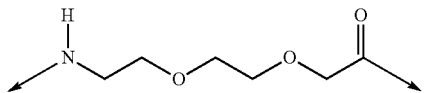

2-Fua: β-(2-furyl)-alanine; Gaba: 4-aminobutyric acid; Gln or Q: glutamine; Glu or E: glutamic acid; Gly or G: glycine; His or H: histidine; 3-Hyp: trans-3-hydroxy-L-proline, i.e., (2S,3S)-3-hydroxypyrrolidine-2-carboxylic acid; 4-Hyp: 4-hydroxyproline, i.e., (2S,4R)-4-hydroxypyrrolidine-2-carboxylic acid; Ile or I: isoleucine; Leu or L: leucine; hLeu: homoleucine; Lys or K: lysine; Met or M: methionine; β-hMet: β-homomethionine; 1-Nal: β-O-naphthylalanine; 2-Nal: β-(2-naphthylalanine; Nip: nipecotic acid; Nle: norleucine; Oic: octahydroindole-2-carboxylic acid; Orn: ornithine; 2-Pal: β-(2-pyridiyl)alanine; 3-Pal: β-(3-pyridiyl)alanine; 4-Pal: β-(4-pyridiylalanine; Pen: penicillamine; Phe or F: phenylalanine; hPhe: homophenylalanine; Pro or P: proline; hPro: homoproline.

Ser or S: serine; Tle: tert-Leucine; Taz: β-(4-thiazolyl)alanine; 2-Thi: β-(2-thienyl)alanine; 3-Thi: β-(3-thienyl)alanine; Thr or T: threonine; Trp or W: tryptophan; Tyr or Y: tyrosine; D-(Et)Tyr has a structure of:

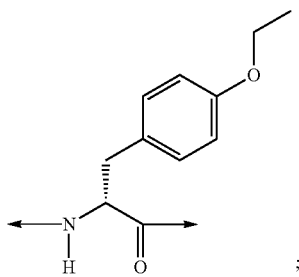

Val or V: valine.

The following are definitions of terms used in this specification. The initial definition provided for a group or term herein applies to that group or term throughout the present specification, individually or as part of another group, unless otherwise indicated. Unless defined otherwise, all technical and scientific terms used herein have the same meaning as commonly understood by one of ordinary skill in the art to which this invention belongs.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When a subscript is used with reference to an alkyl or other group, the subscript refers to the number of carbon atoms that the group may contain. The term "substituted alkyl" refers to an alkyl group as defined above having one, two or three substituents selected from the group consisting of halo, amino, cyano, keto (=O), —$OR_a$, —$SR_a$, —$NR_aR_b$, —(C=O)$R_a$, —$CO_2R_a$, —C(=O)$NR_aR_b$, —$NR_aC$(=O)$R_b$, —$NR_aCO_2R_b$, —OC(=O)$R_a$, —OC(=O)$NR_aR_b$, —$NR_cC$(=O)$NR_aR_b$, —$NR_aSO_2R_d$, —$SO_2R_d$, —$SO_3R_d$, cycloalkyl, aryl, heteroaryl, or heterocycle, wherein the groups $R_a$, $R_b$, and $R_c$ are selected from hydrogen, ($C_1$-$C_6$)alkyl, aryl, heteroaryl, heterocycle, cycloalkyl, or ($C_1$-$C_6$)alkyl substituted with halogen, hydroxy, methoxy, nitro, amino, cyano, —(C=O)H, —$CO_2H$, —(C=O)alkyl, —$CO_2$alkyl, —NH(alkyi), —NH(cycloalkyl), —N(alkyl)$_2$, carboxy, acyl, —C(=O)H, —C(=O)phenyl, —$CO_2$-alkyl, cycloalkyl, —(C=O)$NH_2$, —(C=O)NH(alkyl), —(C=O)NH(cycloalkyl), —(C=O)N(alkyl)$_2$, —C(=O)—(CH$_2$)$_{1-2}$NH$_2$, —C(=O)—(CH$_2$)$_{1-2}$NH(alkyl), —C(=O)—(CH$_2$)$_{1-2}$N(alkyl)$_2$, —NH—CH$_2$-carboxy, —NH—CH$_2$—CO$_2$-alkyl, phenyl, benzyl, phenylethyl, or phenyloxy. The group $R_d$ may be selected from the same groups as $R_a$, $R_b$ and $R_c$ but is not hydrogen. Alternatively, the groups $R_a$ and $R_b$ may together form a heterocyclo or heteroaryl ring. It should be understood that when a substituted alkyl group is substituted with an aryl, cycloalkyl, heteroaryl, or heterocyclo, such rings are as defined below and thus may have one to three substituents as set forth below in the definitions for these terms. When the term "alkyl" is used as a suffix following another specifically named group, e.g., arylalkyl or heteroarylalkyl, the term defines, with more specificity, at least one of the substituents that the substituted alkyl will contain. For example, arylalkyl refers to an aryl bonded through an alkyl, or in other words, a substituted alkyl group having from 1 to 12 carbon atoms and at least one substituent that is aryl (e.g., benzyl or biphenyl). "Lower arylalkyl" refers to substituted alkyl groups having 1 to 4 carbon atoms and at least one aryl substituent. The term "alkenyl" refers to straight or branched chain hydrocarbon groups having 2 to 12 carbon atoms and at least one double bond. Alkenyl groups of 2 to 6 carbon atoms and having one double bond are most preferred. The term "alkynyl" refers to straight or branched chain hydrocarbon groups having 2 to 12 carbon atoms and at least one triple bond. Alkynyl groups of 2 to 6 carbon atoms and having one triple bond are most preferred. A substituted alkenyl or alkynyl will contain one, two, or three substituents as defined above for alkyl groups. The term "alkylene" refers to bivalent straight or branched chain hydrocarbon groups having 1 to 12 carbon atoms, preferably 1 to 8 carbon atoms, e.g., {—CH$_2$—}$_n$, wherein n is 1 to 12, preferably 1 to 8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above. Substituted alkylene, alkenylene, and alkynylene groups may have substituents as defined above for substituted alkyl groups. The term "alkoxy" refers to the group OR$_e$ wherein R$_e$ is alkyl, substituted alkyl, alkenyl, substituted alkenyl, alkynyl, substituted alkynyl, heterocycle, or cycloalkyl. Thus, an alkoxy includes such groups as methoxy, ethoxy, cyclopropyloxy, pyrrolidinyloxy, and so forth. The term "aryloxy" refers to the groups O(aryl) or O(heteroaryl), wherein aryl and heteroaryl are as defined below.

The term "alkylthio" refers to an alkyl or substituted alkyl group as defined above bonded through one or more sulfur (—S—) atoms, e.g., —S(alkyl) or —S(alkyl-R$_a$).

The term "alkylamino" refers to an alkyl or substituted alkyl group as defined above bonded through one or more nitrogen (—NR$_f$—) groups, wherein R$_f$ is hydrogen, alkyl, substituted alkyl, or cycloalkyl. The term "acyl" refers to an alkyl or substituted alkyl group as defined above bonded through one or more carbonyl {—C(=O)—} groups. When the term acyl is used in conjunction with another group, as in acylamino, this refers to the carbonyl group {—C(=O)} linked to the second named group.

Thus, acylamino refers to —C(=O)NH$_2$, substituted acylamino refers to the group —C(=O)NRR, and acylaryl refers to —C(=O)(aryl).

The term "aminoacyl" refers to the group —NR$_f$C(=O)R$_g$, wherein R$_g$ is hydrogen, alkyl, or substituted alkyl, and R$_f$ is as defined above for alkylamino groups.

The term "halo" or "halogen" refers to chloro, bromo, fluoro and iodo. Unless otherwise indicated, any haloalkyl, haloalkoxy or haloalkylthio group contains one or more halo atoms which halo atoms may be the same or different.

The term "carboxy" when used alone refers to the group CO$_2$H. Carboxyalkyl refers to the group CO$_2$R, wherein R is alkyl or substituted alkyl.

The term "sulphonyl" refers to a sulphoxide group (i.e., —S(O)$_{1-2}$—) linked to an organic radical including an alkyl, alkenyl, alkynyl, substituted alkyl, substituted alkenyl, or substituted alkynyl group, as defined above. The organic radical to which the sulphoxide group is attached may be monovalent (e.g., —SO$_2$-alkyl), or bivaleht (e.g., —SO$_2$-alkylene, etc.).

The term "cycloalkyl" refers to substituted and unsubstituted monocyclic or bicyclic hydrocarbon groups of 3 to 9 carbon atoms which are, respectively, fully saturated or partially unsaturated, including a fused aryl ring, for example, an indan. A cycloalkyl group may be substituted by one or more (such as one to three) substituents selected from alkyl, substituted alkyl, aminoalkyl, halogen, cyano, nitro, trifluoromethyl, hydroxy, alkoxy, alkylamino, sulphonyl, —SO$_2$(aryl), —CO$_2$H, —CO$_2$-alkyl, —C(=O)H, keto, —C(=O)—(CH$_2$)$_{1-2}$NH$_2$, —C(=O)—(CH$_2$)$_{1-2}$NH(alkyl), —C(=O)—(CH$_2$)$_{1-2}$N(alkyl)$_2$, acyl, aryl, heterocycle, heteroaryl, or another cycloalkyl ring of 3 to 7 carbon atoms. The term "cycloalkylene" refers to a cycloalkyl forming a link or spacer between two other groups, i.e., a cycloalkylene is a cycloalkyl that is bonded to at least two other groups. The term cycloalkyl includes saturated or partially unsaturated carbocyclic rings having a carbon-carbon bridge of three to four carbon atoms or having a benzene ring joined thereto. When the cycloalkyl group is substituted with a further ring, said further ring may have one to two substituents selected from R$_k$, wherein R$_k$ is lower alkyl, hydroxy, lower alkoxy, amino, halogen, cyano, trifluoromethyl, trifluoromethoxy, nitro, and lower alkyl substituted with one to two hydroxy, lower alkoxy, amino, halogen, cyano, trifluoromethyl, trifluoromethoxy, and/or nitro.

The term "aryl" refers to substituted and unsubstituted phenyl, 1-naphthyl and 2-naphthyl, with phenyl being preferred. The aryl may have zero, one, two or three substituents selected from the group consisting of alkyl, substituted alkyl, alkoxy, alkylthio, halo, hydroxy, nitro, cyano, amino, trifluoromethyl, trifluoromethoxy, sulphonyl, —SO$_2$(aryl), —NH(alkyl), —NH(cycloalkyl), —N(alkyl)$_2$, carboxy, acyl, —C(=O)H, —C(=O)phenyl, —CO$_2$-alkyl, cycloalkyl, —C(=O)NH$_2$, —C(=O)NH(alkyl), —C(=O)NH(cycloalkyl), —C(=O)N(alkyl)$_2$, —NH—CH$_2$-carboxy, —NH—CH$_2$—CO$_2$-alkyl, —C(=O)—(CH$_2$)$_{1-2}$NH$_2$, —C(=O)—(CH$_2$)$_{1-2}$NH(alkyl), —C(=O)—(CH$_2$)$_{1-2}$N(alkyl)$_2$, phenyl, benzyl, phenylethyl, phenyloxy, phenylthio, heterocyclo, heteroaryl, or a (C$_3$-C$_7$)cycloalkyl ring. The term "arylene" refers to an aryl as defined above forming a link or spacer between two other groups, i.e., an arylene is an aryl that is bonded to at least two other groups. When the aryl group is substituted with a further ring, said further ring may have one to two substituents selected from R$_k$, wherein R$_k$ is defined as above.

The term "heterocyclo" or "heterocycle" refers to substituted and unsubstituted non-aromatic 3- to 7-membered monocyclic groups, 7- to 11-membered bicyclic groups, and 10- to 15-membered tricyclic groups which have at least one heteroatom (O, S or N) in at least one of the rings. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quatemized. The heterocyclo group may be attached at any available nitrogen or carbon atom. The heterocyclo ring may contain one, two or three substituents selected from the group consisting of halo, amino, cyano, alkyl, substituted alkyl, trifluoromethyl, trifluoromethoxy, sulphonyl, —SO$_2$(aryl), —NH(alkyl), —NH(cycloalkyl), —N(alkyl)$_2$, alkoxy, alkylthio, hydroxy, nitro, phenyl, benzyl, phenylethyl, phenyloxy, phenylthio, carboxy, —CO$_2$-alkyl, cycloalkyl, —C(=O)H, acyl, —C(=O)NH$_2$, —C(=O)NH(alkyl), —C(=O)NH(cycloalkyl), —C(=O)N(alkyl)$_2$, —NH—CH$_2$-carboxy, —NH—CH$_2$—CO$_2$-alkyl, —C(=O)—(CH$_2$)$_{1-2}$NH$_2$, —C(=O)—(CH$_2$)$_{1-2}$NH(alkyl), —C(=O)—(CH$_2$)$_{1-2}$N(alkyl)$_2$, heterocyclo, heteroaryl, a (C$_3$-C$_7$)cycloalkyl ring, keto, =N—OH, =N—O-lower alkyl, or a five or six-membered ketal, i.e., 1,3-dioxolane or 1,3-dioxane. When the heterocyclo group is substituted with a further ring, said further ring may have one to two substituents selected from R$_k$, wherein R$_k$ is defined as above. Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain one, two or three substituents selected from the group consisting of halo, amino, cyano, alkyl, substituted alkyl, trifluoromethyl, trifluoromethoxy, sulphonyl, —SO$_2$(aryl), —NH(alkyl), —NH(cycloalkyl), —N(alkyl)$_2$, alkoxy, alkylthio, hydroxy, nitro, phenyl, benzyl, phenylethyl, phenyloxy, phenylthio, carboxy, —CO$_2$-alkyl, cycloalkyl, —C(=O)H, acyl, —C(=O)NH$_2$, —C(=O)NH(alkyl), —C(=O) NH(cycloalkyl), —C(=O)N(alkyl)$_2$, —NH—CH$_2$-carboxy, —NH—CH$_2$—CO$_2$-alkyl, —C(=O)—(CH$_2$)$_{1-2}$NH$_2$, —C(=O)—(—CH$_2$)$_{1-2}$NH(alkyl), —C(=O)—(CH$_2$)$_{1-2}$N (alkyl)$_2$, heterocylco, heteroaryl, or a (C$_3$-C$_7$)cycloalkyl ring. The heterocyclo ring may have a sulfur heteroatom that is substituted with one or more oxygen (=O) atoms. Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like. Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like. Exemplary tricyclic heteroaryl groups include carbazolyl, benzidolyl, phenanthrollinyl, acridinyl, phenanthridinyl, xanthenyl and the like.

The peptide of the drug composition of the present invention may be in the form of a salt or as a free base. It may be present in the drug composition at a concentration ranging from about 20 to about 70% (w/w) of the microparticles composition. In a preferred embodiment, the peptide of the drug composition is present at concentration from 20 to 70% (w/w) of the microparticles. In a preferred embodiment, the peptide of the drug composition is a ligand of melanocortin MC4 receptor and is present at a concentration ranging between 25 and 60% (w/w) and more preferably at a concentration from 30 to 50% of the microparticles.

A drug composition according to the present invention comprises a polymer which is biocompatible and water-soluble (miscible at least at the concentration of 5% in water at 25° C.). The biocompatible and water-soluble polymer may be selected from mono- or poly-saccharides, polyvinylpyrrolidone (PVP), cellulose and cellulose derivatives, natural or recombinant proteins and protein derivatives. The mono- or poly-saccharides may be selected from hyaluronic acid or a salt thereof, dextrans or modified dextrans, chitosans, starch or modified starches, alginic acid or salts thereof. The biocompatible water-soluble polymer may be biodegradable. When the biocompatible polymer is biodegradable, it may be selected from hyaluronic acid or a salt thereof, dextrans or modified dextrans, alginic acid or salts thereof. The biocompatible water-soluble polymer may be a biopolymer. When the biodegradable polymer is a biopolymer, it may be selected from hyaluronic acid or inorganic salts thereof such as sodium hyaluronate, alginic acid or inorganic salts thereof such as sodium alginate, or chitosan.

In a preferred embodiment, the biocompatible water-soluble polymer is biodegradable and more preferably it is a biopolymer.

In a preferred embodiment, the biocompatible water-soluble polymer is a polysaccharide. In another preferred embodiment, the biocompatible water-soluble polymer is a polysaccharide having a molecular weight (Mw) lower than 2000 kDa, more preferably lower than 1800 kDa.

Preferably, the biocompatible water-soluble polymer is a high molecular weight polysaccharide.

In another preferred embodiment; the biocompatible water-soluble polymer is a polysaccharide having a molecular weight (Mw) higher than 1000 kDa, more preferably higher than 1200 kDa.

In another preferred embodiment, the biocompatible water-soluble polymer is a polysaccharide having a molecular weight (Mw) between 1000 kDa and 2000 kDa, and more preferably between 1200 kDa and 1800 kDa.

In a preferred embodiment, the biocompatible water-soluble polymer is a polysaccharide selected from hyaluronic acid or a salt thereof. In another preferred embodiment, the biocompatible water-soluble polymer is a polysaccharide selected from salts of hyaluronic acid and more preferably is sodium hyaluronate (SH).

In a preferred embodiment, the biocompatible water-soluble polymer is a polysaccharide selected from salts of hyaluronic acid and having a molecular weight (Mw) between 1000 kDa and 2000 kDa, In a preferred embodiment, the biocompatible water-soluble polymer is sodium hyaluronate (SH), having a molecular weight (Mw) between 1000 kDa and 2000 kDa, more preferably between 1200 kDa and 1800 kDa.

In another preferred embodiment, the weight ratio peptide/polymer in the microparticles is comprised between 3:1 and 1:4.

In a more preferred embodiment, the peptide is the peptide 1 as described above or a pharmaceutically acceptable salt thereof, the biocompatible water-miscible polymer is sodium hyaluronate and the weight ratio is between 3 to 0.25, preferably between 1.5 and 0.33, and more preferably between 1 and 0.33.

The microparticles may optionally contain additives such as surfactants. These additives include fatty acids and salts thereof, polyols, polyoxyethers, poloxamers, polysorbates and polyoxyethylene fatty acid esters.

In another preferred embodiment, the microparticles contain any additive. In another preferred embodiment, the microparticles contain any surfactant. In another preferred embodiment, the microparticles contain no surfactant. In a preferred embodiment, the microparticles comprise only the peptide as active substance and the biocompatible polymer.

Microparticles of the present invention may be prepared by mixing the peptide, the water-soluble polymer and the optional additives (if any) in water, then spray dried. The recovered powder may be filled into vials and gamma-irradiated to get a sterile injectable product.

In another aspect of the present invention, the microparticles of the present invention are obtained by spray-drying, preferably at a temperature between 130 and 170° C., and more preferably by organic solvent-free spray drying.

The average size of microparticle thus obtained ranges from 2 to 50 μm preferably from 5 to 30 μm and more preferably from 6 to 24 μm.

Another object of the present invention is an injectable formulation comprising the drug composition as described above, said drug composition being suspended in an injectable liquid vehicle.

The injectable liquid vehicle may be selected of from propylene glycol, polyethylene glycol, vegetable oil, mineral oil, squalene, glycerol, mono-, di- or tri-glycerides or mixtures of thereof. The suspension medium for administration of the drug composition can be a non aqueous injectable liquid of low viscosity such as mixtures of medium chain triglycerides (fatty acid esters of glycerol). Preferred medium chain triglycerides are Miglyol® 812 (from Sasol GmbH, Germany), Labrafac® WL1349 (caprylic acid triglyceride from Gattefosse company, France), or Lipoid MCT (from Lipoid company, Germany) The non-aqueous injectable suspension medium may contain further auxiliaries such as suitable surfactants (Poloxamer 188, Solutol® HS 15, Cremophor® Tween® 20, 40 and 80, lecithin).

In a preferred embodiment, the injection medium is a lipophilic suspension medium.

The injectable liquid vehicle used as the suspension medium may be selected from mono-, di- and tri-glyceride or a mixture thereof.

In another preferred embodiment, the vehicle of the injectable formulation is a mono-, di- and tri-glyceride or a mixture thereof. In a more preferred embodiment, the vehicle is a triglyceride or a mixture thereof, and more preferably a medium-chain triglyceride (MCT) or a mixture thereof.

The medium-chain triglyceride (MCT) may be selected from Miglyol® 810 (caprylic/capric triglyceride; Register Number (RN)=8540909-2), Miglyol® 812 (caprylic/capric triglyceride; Register Number (RN)=8540909-2), Miglyol® 818 (Register Number (RN)=308067-10-9), Miglyol® 829 (Register Number (RN)=97708-73-1), Miglyol® 840 (Register Number (RN)=77466-09-2), or a mixture thereof. In a more preferred embodiment, the triglyceride used as a liquid vehicle in the injectable formulation is Miglyol® 812.

The injection formulation may comprise other additives such a dispersing agent. Dispersing agents include amphiphilic lipids, phospholipids, fatty acids, polysaccharides, polyols, polyoxyethers, poloxamers, polysorbates and polyoxyethylene fatty acid esters.

The dispersing agent may be selected for instance from phospholipids and preferably from lecithin. The concentration of the dispersing agent (if any) is lower than 5% (w/w) of the suspension medium.

In a preferred embodiment, the vehicle of the injectable formulation comprises a dispersing agent. In a preferred embodiment, the vehicle of the injectable formulation comprises a dispersing agent having a hydrophile-lipophile balance (HLB) lower than 17. In a more preferred embodiment, the dispersing agent is selected from lecithin.

In a more preferred embodiment, the vehicle is a mixture of medium chain triglyceride (MCT) and lecithin, and more preferably, the vehicle is a mixture of Miglyol® 812 and lecithin.

In a more preferred embodiment, the vehicle is a mixture of Miglyol® 812 and lecithin, and the weight ratio lecithin/Miglyol® 812 ranges between about 0.1% (0.1±0.1) and 2% (2±0.1), more preferably between 0.1 and 1%.

In a more preferred embodiment, the injectable formulation comprises:
  microparticles comprising only the peptide 1 as active ingredient and a biopolymer, and
  a mixture of a medium chain triglyceride and a dispersing agent as the suspension medium; and more preferably
  microparticles comprising only the peptide 1 as active ingredient and sodium hyaluronate as biopolymer, and
  a mixture of a medium chain triglyceride and lecithin as the suspension medium.

The injection formulation may be prepared by mixing the microparticles and the suspension medium. The different constituents of the suspension medium may be mixed then sterilized by filtration for instance and filled in a vial. The microparticles can be filled into vials and then sterilized by gamma-irradiation. The microparticles and the suspension medium may be extemporaneously mixed so as to suspend the microparticles in the vehicle for injection before administration.

The injectable formulation according to the present invention may be useful for a parenteral administration with a sustained-release of the peptide for at least 3 hours. The injectable formulation according to the present invention may be useful for a parenteral administration with a sustained-release of the peptide for at least 4 hours, 5 hours, 6 hours, 12 hours or 24 hours. In a preferred embodiment, an injection formulation according to the present invention allows a sustained release for at least 3 hours. In another preferred embodiment, an injection formulation according to the present invention allows a sustained release for at least 6 hours. In a more preferred embodiment, an injection formulation according to the present invention allows a sustained release for at least 12 hours and more preferably 24 hours.

An injectable formulation according to the present invention is particularly useful to treat disorders of body weight such as obesity and cachexia.

The following examples are presented to illustrate the above procedures and should not be considered as limiting the scope of the invention.

Experimental Part

EXAMPLE 1

Preparation of Microparticles

Microparticles were obtained by spray drying using a mini spray dryer such as BUCHI 190, Micro SD or BUCHI B-290 spray-dryer.

Sodium hyaluronate (SH) was dissolved aseptically in water for injection (WFI) (=0.4% w/v) with a magnetic stirrer for 2 h.

The peptide 1 was precisely weighed and dissolved in water with a magnetic stirrer.

Homogenisation of the final preparation was completed using an Ultraturax turbine for 30 min. The pH of the final blend ranged between 4 and 5.

A feed stock at a solid concentration not higher than 0.33% w/v, containing 3.325 g of total solids per liter was prepared in order to allow efficient nebulization of the blend. The homogeneity of this preparation was maintained by applying a moderate stirring while feeding the spray dryer.

Operational spray-drying parameters used were as follows: Inlet temperature: 130-170° C.; Feed flow rate: 5-6 mL/min; Atomiser gas rate: 2-4 kg/h; Aspiration: 30 m$^3$/h; Air flow rate: 650-700 NI/h.

The recovered powder was filled into vials and can be gamma-irradiated at 25 kGy.

Preparation of the Injectable Formulation

The powder was suspended in a vehicle containing 99% MCT (Miglyol® 812N) and 1% lecithin (Epikuron 200) before use. The vehicle was manufactured as follows: lecithin was dissolved in Miglyol® 812 N at 55° C.±5° C. under magnetic stirring, until a homogeneous dispersion is obtained. The obtained solution was then filtered on 0.22 µm filter for sterilization before aseptic vial filling.

EXAMPLE 2

Injectability Study and Particle Size Distribution Measurement

The injectability study was performed on an injection composition comprising:
  microparticles of peptide 1/sodium hyaluronate 40/60 (w/w), and
  a suspension medium containing Miglyol® 812 and lecithin (1%).

The microparticles were manufactured as described in example 1, using a larger spray-drying equipment, namely the ASD-1 spray-dryer equipment. The microparticles thus obtained were characterized as regards their particle size distribution (PSD) before and after applying a dry sieving step (Table 1)

TABLE 1

| | Microparticle size distribution - Batch C15 | |
|---|---|---|
| | 1 minute ultrasound - no sieving | after sieving on 63 μm mesh |
| D10 (μm) | 4.79 | 8.84 |
| D50 (μm) | 21.33 | 32.23 |
| D90 (μm) | 68.88 | 64.94 |
| Average size (μm) | 30.63 | 35.11 |

A good dispersion was obtained without the need for ultrasound treatment for sieved microparticles.

The injectability was evaluated using a traction/compression machine which measures the injection strength during the extrusion of the formulation from a 1 mL syringe fitted with a needle. The maximal tolerated strength is 15 N, and the tested needle diameters acceptable for a daily subcutaneous injection are at least 25-27 Gauge. The injectability was evaluated at 50 mg/mL or 20 mg/mL active for lecithin-free microparticle prototypes. The injectability results are summarized in Table 2 below.

TABLE 2

| | Prototype | | |
|---|---|---|---|
| | 1 | 2 | 3 |
| Pure Peptide theoretical content (% w/w) | 30 | 40 | 30 |
| SH (% w/w) | 61.4 | 48.5 | 60 |
| Supension medium | Miglyol ® 812 N | Miglyol ® 812 N + 1% Lecithin | Miglyol ® 812 N + 1% Lecithin | Miglyol ® 812 N + 1% Lecithin |
| Active concentration (mg/mL) | 50 | 50 | 50 | 20 |
| Powder quantity per mL (mg) | 167 | 167 | 125 | 70 |
| Injection force for 25 G needle (N) | <15 | | | |

For such a high microparticle content in the oily injectable vehicle, the injection of the microparticle suspension through a 25 Gauge needle allowed to deliver the suspension with an acceptable injection force when prototype microparticles were manufactured with a 30 to 40% peptide content.

The results obtained for the "manual" injectability testing are presented in Table 3.

TABLE 3

| | Concentration of | Injectability | |
|---|---|---|---|
| Batch C15 | peptide (mg/mL) | 25 G | 27 G |
| prior to sieving | 10 | yes | no |
| | 20 | yes | no |
| post sieving | 20 | yes | yes |

"yes" means that the suspension is injectable through the needle with the specified gauge number; "no" means that the suspension is not injectable through the needle with the specified gauge number.

This injectability study showed very promising results from the large scale material after the dry sieving step on a 63 μm mesh size sieve. At 20 mg/mL, the suspension was injectable through a 27 G needle.

EXAMPLE 3

In Vivo Testing

Figure 2:
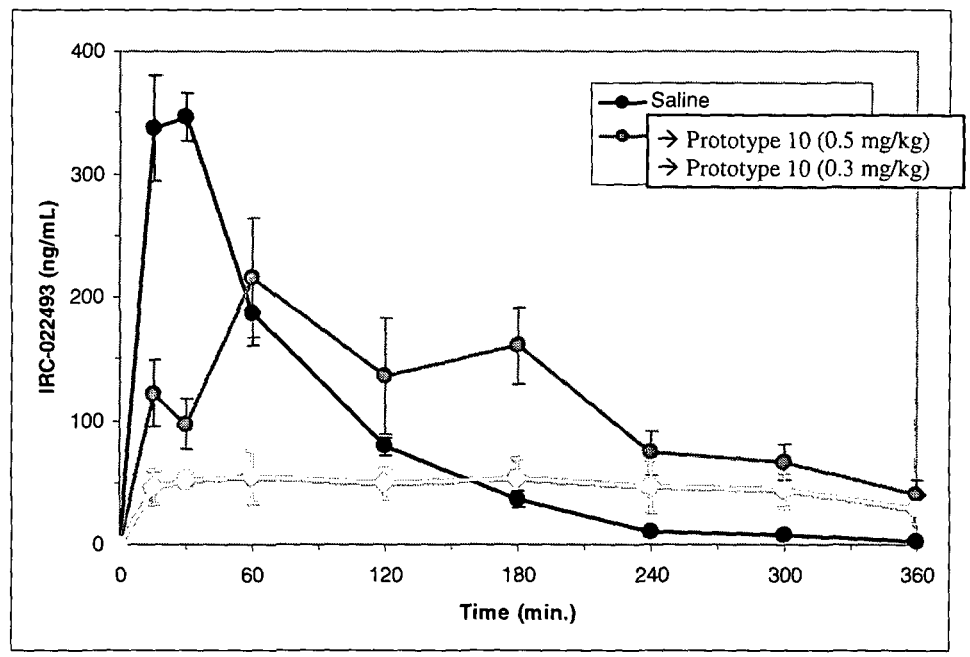
FIG. 2 depicts the pharmacokinetic profiles obtained following the administration of a composition comprising microparticles of a peptide having a dose of 0.5 mg/kg and a composition comprising microparticles of a peptide having a dose of 0.3 mg/kg.

The PK profiles of the selected prototypes with peptide 1 as active ingredient were evaluated in rats (FIGS. 1 and 2). Eight rats divided in two groups of four were used per prototype. Each of them received a subcutaneous injection of microparticles dispersed in a suspension medium (Miglyol® 812 N with or without 1% lecithin filtered through 0.22 μm) at a dose of 0.5 mg/kg and then at 0.3 mg/kg. Blood sampling was performed via a jugular catheter at different time points in each group alternatively. The peptide plasma concentrations were determined by LC-MS technique.

PK values were compared to the one obtained after the injection of the peptide in a saline solution under the same conditions; this was chosen as a reference since the peptide suspended in Miglyol® 812 N cannot be injected because it visually leads to highly heterogeneous, poorly stable suspensions. The PK parameters of microparticles and saline reference are shown in Table 4 below.

TABLE 4

| Composition | # | $C_{max}$ (ng/mL) | % $C_{max}$ vs. Ref | $AUC_{last}$ (min * ng/mL) | % $AUC_{last}$ vs. Ref. | MRT (min) | $T_{max}$ (min) | $T_{1/2}$ (min) |
|---|---|---|---|---|---|---|---|---|
| Reference NaCl 0.9% | / | 346 | / | 29.6 | / | 75 | 30 | 49.4 |
| Microparticles: Peptide/SH: 1:2 Vehicle: Miglyol | 2 | 162 | 47 | 41.6 | 141 | 187 | 120 | 71 |
| Peptide/SH 1:2 Vehicle: Miglyol + 1% Lecithin | 4 | 239 | 69 | 53.3 | 180 | 171 | 60 | 90 |
| Microparticles: Peptide/SH/Lecithin 1:1/3:2 Vehicle: Miglyol | 10 | 216 | 62 | 49.5 | 167 | 215 | 60 | 129 |

($C_{max}$: maximum plasma concentration of the drug appearing in the pK profile; AUC: Area Under the Curve; MRT: Medium Residence Time; $T_{max}$: time corresponding to the $C_{max}$ value; $T_{1/2}$: half life).

Then, a new in vivo test was performed in order to evaluate the possibility to inject a lower dose for the same drug exposure. The in vivo testing in rats was performed using prototype microparticles at the dose of 0.3 mg/kg (60% of the initial dose). The PK profile and parameters are presented in FIG. 2 (PK profile in rats–270 nmoles/kg, 0.3 mg/kg vs 450 nmole/kg, 0.5 mg/kg, SC) and Table 5 (PK parameters of microparticles and saline reference) respectively.

TABLE 5

| Composition | $C_{max}$ (ng/mL) | % $C_{max}$ vs. Ref | $AUC_{last}$ (min * ng/mL) | % $AUC_{last}$ vs. Ref. | MRT (min) | $T_{max}$ (min) | $T_{1/2}$ (min) |
|---|---|---|---|---|---|---|---|
| Reference NaCl 0.9% 0.5 mg/kg | 346 | / | 29.6 | / | 75 | 30 | 49 |
| Prototype 10 0.5 mg/kg | 216 | 62 | 49.5 | 167 | 215 | 60 | 129 |
| Prototype 10 0.3 mg/kg | 54.6 | 16 | 26.7 | 90 | 360 | 60 | 218 |

The release profile tends towards a zero-order kinetics over at least 6 hours presenting a pump-like behavior with the same exposure than the one obtained with the peptide in saline at a higher dose (0.5 mg/kg). This suggests the possibility of a lower therapeutic dose for the same drug exposure and the possibility to avoid side effects and increase the tolerance of the treatment.

This PK study demonstrates the sustained release (SR) properties.

EXAMPLE 4

Stability Study

The stability study was conducted with peptide 1 (under the acetate salt form). The results are shown in Table 6.

TABLE 6

| Example | Timepoint | Purity (%) | Deviation/ T0 (%) | Sum of impurities (%) |
|---|---|---|---|---|
| Peptide/ SH1700 51.5/48.5 | T0 | 98.4 | / | / |
|  | 5M, 5° C. | 97.2 | −1.21 | 1.7 |
|  | 13M, 5° C. | 97.4 | 1.06 | 1.6 |
| Peptide/ SH1700 38.5/61.5 | T0 | 97.5 | / | 1.8 |
|  | 5M, 5° C. | 96.7 | −0.81 | 1.8 |
|  | 13M, 5° C. | 96.9 | −0.63 | 1.8 |
| Peptide/SH 50/50 | T0 | 97.3 | / | 2.0 |
|  | 4.5M, 5° C. | 97.5 | 0.21 | 2.2 |
|  | 4.5M, 25° C./60% RH | 97.3 | 0.00 | 2.3 |
|  | 4.5M, 40° C./75% RH | 96.8 | −0.51 | 2.7 |
| Peptide/SH 40/60 | T0 | 97.4 | / | 2.3 |
|  | 4.5M, 5° C. | 97.4 | 0.00 | 2.1 |
|  | 4.5M, 25° C./60% RH | 97.1 | −0.31 | 2.2 |
|  | 4.5M, 40° C./75% RH | 96.8 | −0.62 | 2.6 |
| Peptide/ Dextran 40/60 | T0 | 29.1 | 97.1 | 2.3 |
|  | 4.5M, 5° C. | 30.4 | 97.3 | 2.1 |
|  | 4.5M, 25° C./60% RH | 30.0 | 97.2 | 2.1 |
|  | 4.5M, 40° C./75% RH | 29.5 | 96.9 | 2.5 |
| Peptide/SH/ Kollidon17PF 40/50/10 | T0 | 29.5 | 97.5 | 2.1 |
|  | 4.5M, 5° C. | 30.7 | 97.1 | 2.2 |
|  | 4.5M, 25° C./60% RH | 30.4 | 97.0 | 2.4 |
|  | 4.5M, 40° C./75% RH | 29.4 | 96.6 | 2.6 |

All the examples above were stable for at least 4.5 months at 5° C. and 25° C.

EXAMPLE 5

A composition comprising recombinant human growth hormone (rhGH) and sodium hyaluronate is prepared according to the same preparation process as illustrated in example 1, with rhGH as active ingredient instead of peptide 1.

Recombinant human growth hormone in sodium carbonate buffer was dissolved in water. Sodium hyaluronate was present in the composition at a concentration of 2 mg/mL and rhGH at a concentration of 1 mg/mL. The weight ratio protein/sodium hyaluronate was equal to 0.5.

The composition was then spray dried with an inlet temperature of 130° C.

An ion-exchange high performance liquid chromatography (IE-HPLC) analysis was performed to evaluate the deamination of rhGH and a size-exclusion chromatography high performance liquid chromatography (SEC-HPLC) analysis was performed to evaluate the aggregation of this protein.

Degradation data of the above-mentioned composition before and after spay-drying is shown in Table 7.

TABLE 7

|  |  |  | Batch 1 Flow rate | Batch 2 |
|---|---|---|---|---|
|  |  | Specification | 5 mL/ min | 6 mL/ min |
| Main peak surface area (deamidation) | Before spray-drying | ≥94% | 99.2% | 98.6% |
|  | After spray-drying | ≥94% | 93.8% | 91.2% |
| rhGH monomer (aggregation) | Before spray-drying | ≥98% | 99.9% |  |
|  | After spray-drying | ≥98% | 89.7% | 85.9% |

At 130° C., the protein is not stable in the process according the invention as it is either deaminated or aggregated. Contrary to the peptide 1, rhGH is degraded by the spay-drying process according to the invention.

When the protein is aggregated, there is the formation of oligomers, which means the protein is not active anymore and can become immunogenic.

The process according to the invention is not applicable to proteins.

The invention claimed is:

1. A sustained-release drug composition comprising microparticles comprising:
    a peptide of formula (I), Ac-Arg-c(Cys-D-Ala-His-D-Phe-Arg-Trp-Cys)-NH$_2$ (I), or a pharmaceutically-acceptable salt thereof; and
    a biocompatible water-soluble polymer;
    wherein the peptide and the biocompatible water-soluble polymer are at least 90% by weight of the microparticles and the peptide is present at a concentration of from about 20% to about 70% by weight of the microparticles.

2. The composition of claim 1, wherein the biocompatible water-soluble polymer is a biodegradable water-soluble polymer.

3. The composition of claim 1, wherein the biocompatible water-soluble polymer is a polysaccharide.

4. The composition of claim 3, wherein the polysaccharide has a molecular weight (Mw) lower than 2,000 kDa.

5. The composition of claim 3, wherein the polysaccharide is hyaluronic acid or a salt thereof.

6. The composition of claim 5, wherein the hyaluronic salt is sodium hyaluronate and the weight ratio of the peptide to sodium hyaluronate in the microparticles is from 3 to 0.25.

7. The composition of claim 1, wherein the microparticles are spray-dried.

8. The composition of claim 1, wherein the average size of the microparticles from 2 to 50 µm.

9. The composition of claim 1, wherein the peptide is present at a concentration of from 25 to 60% by weight of the microparticles.

10. The composition of claim 1, wherein the peptide is present at a concentration of from 30 to 50% by weight of the microparticles.

11. The composition of claim 4, wherein the polysaccharide has a molecular weight (Mw) lower than 1,800 kDa.

12. The composition of claim 6, wherein the hyaluronic salt is sodium hyaluronate and the weight ratio of peptide to sodium hyaluronate in the microparticles is from 1 to 0.33.

13. The composition of claim 8, wherein the average size of the microparticles is from 5 to 30 µm.

14. An injectable formulation comprising the composition of claim 1, wherein the composition is suspended in a liquid injectable vehicle used as a suspension medium.

15. The injectable formulation of claim 14, wherein the injectable vehicle is a lipophilic suspension medium.

16. The injectable formulation of claim 14, wherein the injectable vehicle comprises a dispersing agent.

17. The injectable formulation of claim 14, wherein the injectable formulation provides a sustained release of the peptide for at least 3 hours.

18. The injectable formulation of claim 17, wherein the formulation provides a sustained release of the peptide for at least 6 hours.

\* \* \* \* \*